(12) United States Patent
Choi

(10) Patent No.: US 11,642,098 B2
(45) Date of Patent: May 9, 2023

(54) ULTRASONIC IMAGING APPARATUS AND METHOD OF CONTROLLING THE SAME

(71) Applicant: SAMSUNG MEDISON CO., LTD., Gangwon-do (KR)

(72) Inventor: Kwangyeon Choi, Gangwon-do (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 51 days.

(21) Appl. No.: 17/188,080

(22) Filed: Mar. 1, 2021

(65) Prior Publication Data

US 2021/0275135 A1   Sep. 9, 2021

(30) Foreign Application Priority Data

Mar. 6, 2020   (KR) .................. 10-2020-0028303

(51) Int. Cl.
*A61B 8/00* (2006.01)
*A61B 8/08* (2006.01)

(52) U.S. Cl.
CPC ............ *A61B 8/0883* (2013.01); *A61B 8/085* (2013.01); *A61B 8/4488* (2013.01); *A61B 8/461* (2013.01); *A61B 8/54* (2013.01)

(58) Field of Classification Search
CPC ..... A61B 8/0883; A61B 8/085; A61B 8/4488; A61B 8/461; A61B 8/54; A61B 8/02; A61B 8/0866; A61B 8/5223; A61B 8/488
See application file for complete search history.

(56) References Cited

U.S. PATENT DOCUMENTS

| | | |
|---|---|---|
| 2006/0241457 A1 | 10/2006 | Nadadur et al. |
| 2008/0009735 A1 | 1/2008 | Murashita |
| 2010/0185088 A1 | 7/2010 | Perrey et al. |
| 2012/0123267 A1 | 6/2012 | Dow et al. |
| 2013/0085393 A1 | 4/2013 | Schauf et al. |
| 2016/0242732 A1 | 8/2016 | Strassner et al. |
| 2018/0333134 A1 | 11/2018 | Dickie et al. |
| 2019/0343482 A1* | 11/2019 | Abe ............. A61B 8/0866 |

FOREIGN PATENT DOCUMENTS

EP   3571999 A1   11/2019
WO   WO-2021165037 A1 *   8/2021

OTHER PUBLICATIONS

Extended European Search Report dated Aug. 5, 2021 issued in European Patent Application No. 21160775.9.

\* cited by examiner

*Primary Examiner* — Christopher Koharski
*Assistant Examiner* — Taylor Deutsch
(74) *Attorney, Agent, or Firm* — Morgan, Lewis & Bockius LLP

(57) ABSTRACT

The ultrasonic imaging apparatus includes: a display; a probe configured to acquire an ultrasound signal of a heart; and a controller configured to generate an ultrasound image of the heart based on the ultrasound signal, control the display to display the ultrasound image of the heart, and determine an exercise cycle of the heart based on the movement of at least one valve included in the ultrasound image, wherein the ultrasound image comprises an atrium and a ventricle of the heart.

10 Claims, 12 Drawing Sheets

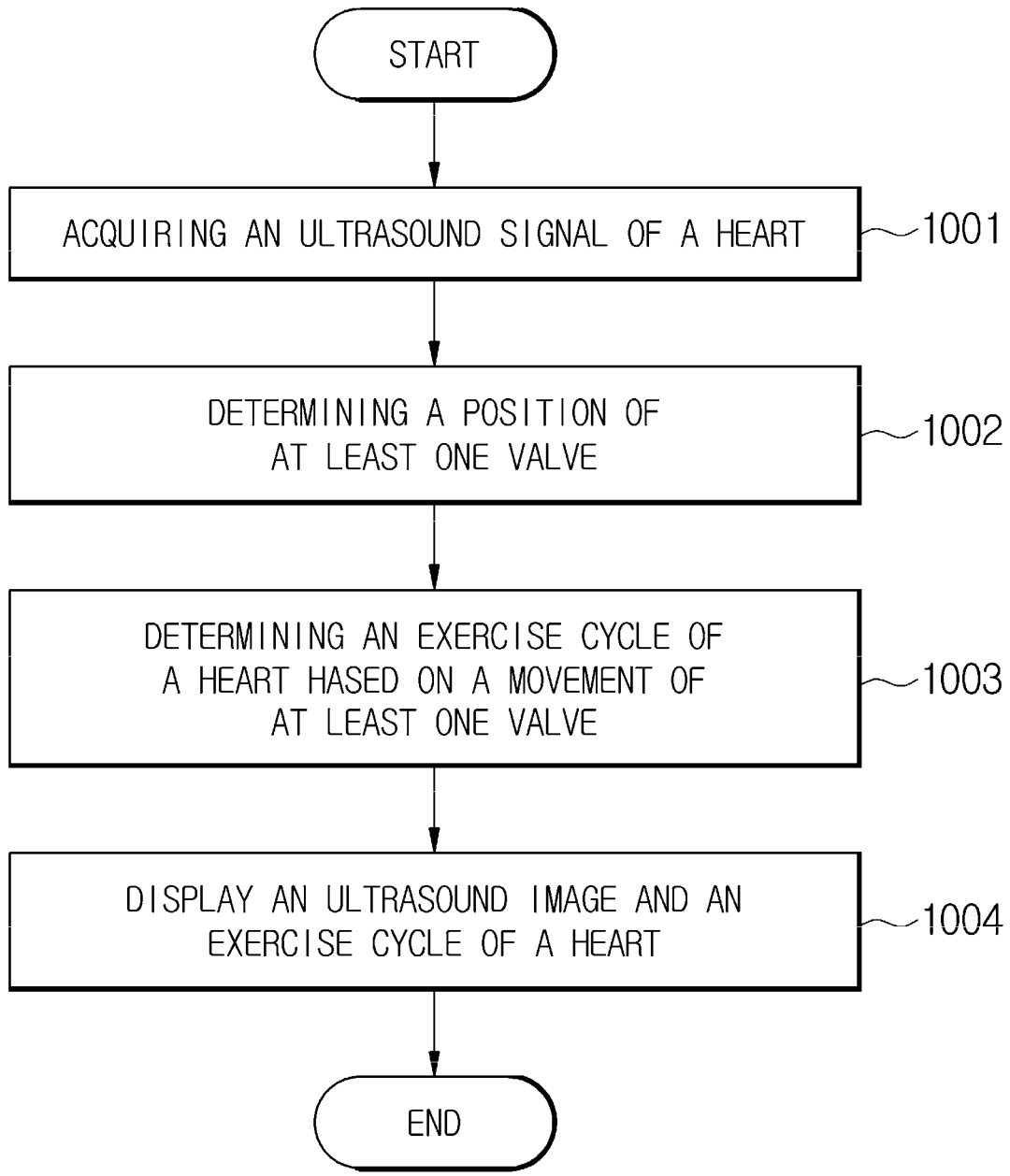

ULTRASONIC IMAGING APPARATUS AND METHOD OF CONTROLLING THE SAME

CROSS-REFERENCE TO RELATED APPLICATION(S)

This application is based on and claims priority under 35 U.S.C. § 119 to Korean Patent Application No. 10-2020-0028303, filed on Mar. 6, 2020 in the Korean Intellectual Property Office, the disclosure of which is incorporated by reference in its entirety.

TECHNICAL FIELD

The disclosure relates to an ultrasound imaging apparatus and a control method for determining an exercise period of a heart using an ultrasound image.

BACKGROUND

The fetal heart rate is an important factor in assessing the health of the fetus during pregnancy.

Methods of measuring the fetal heart rate include a method of using an ultrasound Doppler and a method of measuring a fetal electrocardiogram (ECG).

Methods of measuring fetal ECG include a method of attaching an electrode to the scalp of a fetus by inserting an electrode, and a method of separating the fetal ECG from the maternal abdominal signal. Meanwhile, in clinical practice, a fetal heart rate measurement method using Doppler ultrasound signal is generally used for measuring the fetal heart rate.

However, the method using the Doppler ultrasound signal has a disadvantage in that it is difficult to measure the fetal heartbeat due to errors such as an error between the mother's or fetus' movement and the heart sound and the calculated heart rate.

Therefore, there is a demand for a technology to accurately and efficiently measure the fetal heartbeat.

SUMMARY

Therefore, it is an aspect of the disclosure to provide an ultrasound imaging apparatus and a control method for efficiently determining a heart movement period by using a valve motion included in an ultrasound image of the heart.

Additional aspects of the disclosure will be set forth in part in the description which follows and, in part, will be obvious from the description, or may be learned by practice of the disclosure.

In accordance with an aspect of the disclosure, an ultrasonic imaging apparatus includes: a display; a probe configured to acquire an ultrasound signal of a heart; and a controller configured to generate an ultrasound image of the heart based on the ultrasound signal, control the display to display the ultrasound image of the heart, and determine an exercise cycle of the heart based on the movement of at least one valve included in the ultrasound image, wherein the ultrasound image may comprise an atrium and a ventricle of the heart.

The controller may be configured to determine a position of the at least one valve based on a position of the atrium and the ventricle of the heart.

The controller may be configured to identify the position of the valve of the heart through learning based on the ultrasound image of at least one other heart.

The controller may be configured to determine the position of the valve of the heart based on the position of the annulus included in the heart.

The controller may be configured to generate at least one at least one line corresponding to the position of the valve based on the position of the annulus and determine the movement of the valve based on the at least one line.

The controller may be configured to determine a region of interest (ROI) corresponding to the valve based on a user's command and determine an exercise cycle of the heart based on a brightness value of the ultrasound image corresponding to the region of interest.

The controller may be configured to determine an exercise cycle of the heart based on a change amount of the brightness value.

The ultrasound image of the heart may be include a foramen ovale corresponding to the heart.

The controller may be configured to determine the exercise cycle of the heart based on a movement of the foramen ovale and a movement of the at least one valve.

The controller may be configured to track the position of the heart in real time and determine the position of the at least one valve corresponding to the position on the heart.

In accordance with another aspect of the disclosure, a method of controlling an ultrasonic imaging apparatus includes acquiring an ultrasound signal of a heart; generating an ultrasound image of the heart based on the ultrasound signal; controlling the display to display the ultrasound image of the heart; determining an exercise cycle of the heart based on the movement of at least one valve included in the ultrasound image, wherein the ultrasound image comprises an atrium and a ventricle of the heart.

The method may further include determining a position of the at least one valve based on a position of the atrium and the ventricle of the heart.

The method may further include identifying the position of the valve of the heart through learning based on the ultrasound image of at least one other heart.

The determining a position of the at least one valve may include determining the position of the valve of the heart based on the position of the annulus included in the heart.

The method may further include generate at least one at least one line corresponding to the position of the valve based on the position of the annulus; and The determining an exercise cycle of the heart may include determining the movement of the valve based on the line.

The determining an exercise cycle of the heart may include determining a region of interest (ROI) corresponding to the valve based on a user's command; and determining an exercise cycle of the heart based on a brightness value of the ultrasound image corresponding to the region of interest.

The determining an exercise cycle of the heart may include determining an exercise cycle of the heart based on a change amount of the brightness value over time The ultrasound image of the heart may be including a foramen ovale corresponding to the heart.

The determining an exercise cycle of the heart may include determining the exercise cycle of the heart based on a movement of the foramen ovale and a movement of the at least one valve The method may further include tracking the position of the heart in real time; determining the position of the at least one valve corresponding to the position on the heart

BRIEF DESCRIPTION OF THE DRAWINGS

These and/or other aspects of the disclosure will become apparent and more readily appreciated from the following description of the embodiments, taken in conjunction with the accompanying drawings of which:

FIG. 10 is a flowchart of present of invention.

DETAILED DESCRIPTION

Figure 1:
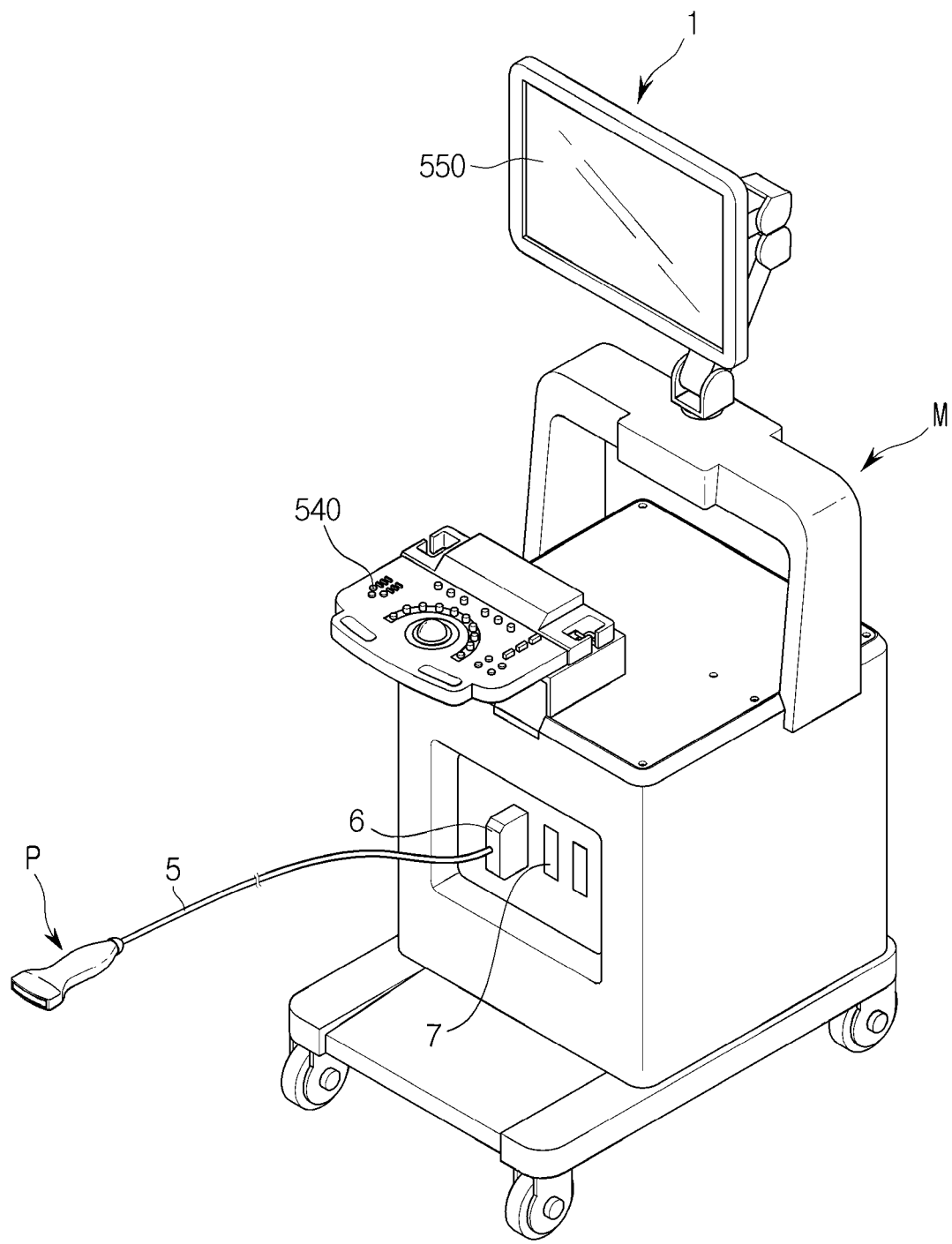
FIG. 1 is a view illustrating an appearance of an ultrasonic imaging apparatus according to exemplary embodiments of the disclosure.

Like reference numerals refer to like elements throughout the specification. Not all elements of embodiments of the disclosure will be described, and description of what are commonly known in the art or what overlap each other in the embodiments will be omitted. The terms as used throughout the specification, such as "~part," "~module," "~member," "~block," etc., may be implemented in software and/or hardware, and a plurality of "~parts," "~modules," "~members," or "~blocks" may be implemented in a single element, or a single "~part," "~module," "~member," or "~block" may include a plurality of elements.

It will be understood that when an element is referred to as being "connected" to another element, it can be directly or indirectly connected to the other element, wherein the indirect connection includes "connection" via a wireless communication network.

Also, when a part "includes" or "comprises" an element, unless there is a particular description contrary thereto, the part may further include other elements, not excluding the other elements.

Further, when it is stated that a layer is "on" another layer or substrate, the layer may be directly on another layer or substrate or a third layer may be disposed therebetween.

It will be understood that, although the terms first, second, third, etc., may be used herein to describe various elements, it should not be limited by these terms.

These terms are only used to distinguish one element from another element.

As used herein, the singular forms "a," "an" and "the" are intended to include the plural forms as well, unless the context clearly indicates otherwise.

An identification code is used for the convenience of the description but is not intended to illustrate the order of each step. Each of the steps may be implemented in an order different from the illustrated order unless the context clearly indicates otherwise.

Hereinafter, the operation principles and embodiments of the disclosure will be described with reference to the accompanying drawings.

Figure 2:
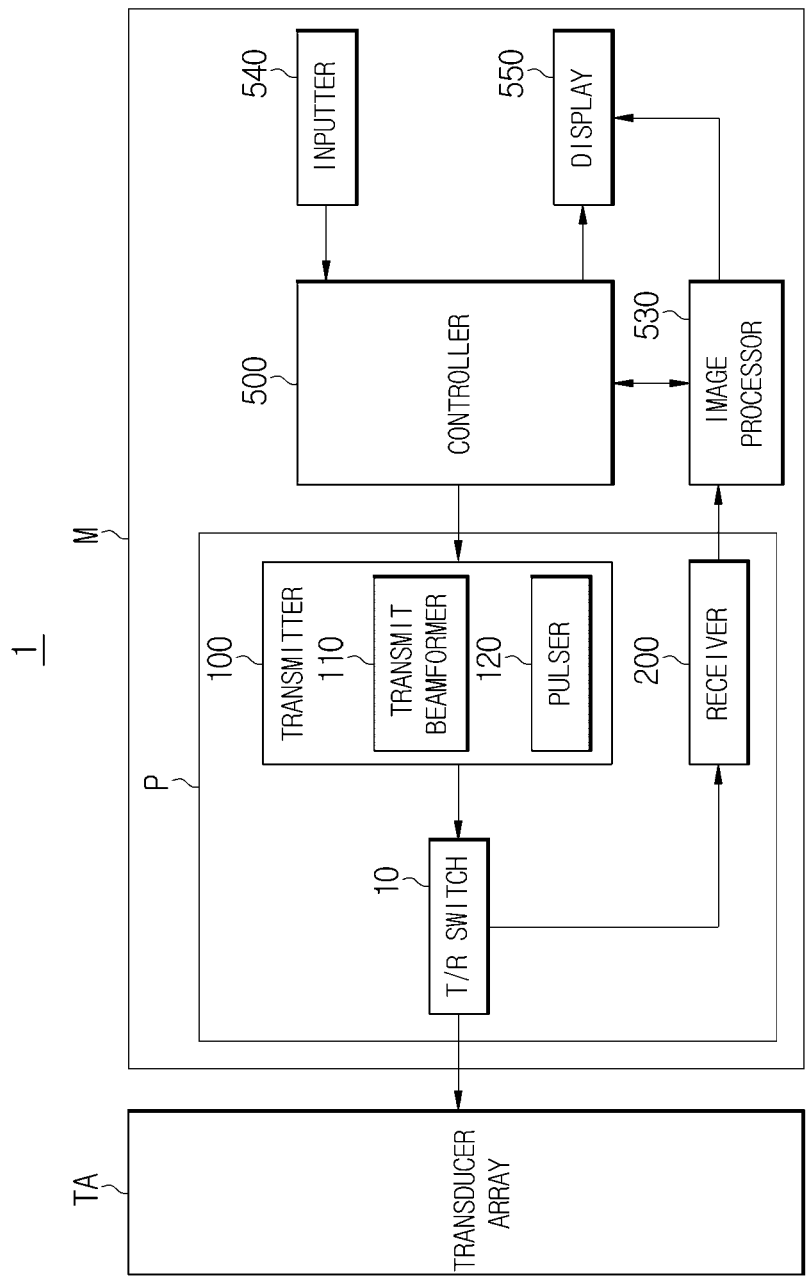
FIG. 2 is a control block diagram of an ultrasonic imaging apparatus according to exemplary embodiments of the disclosure.
Figure 3:
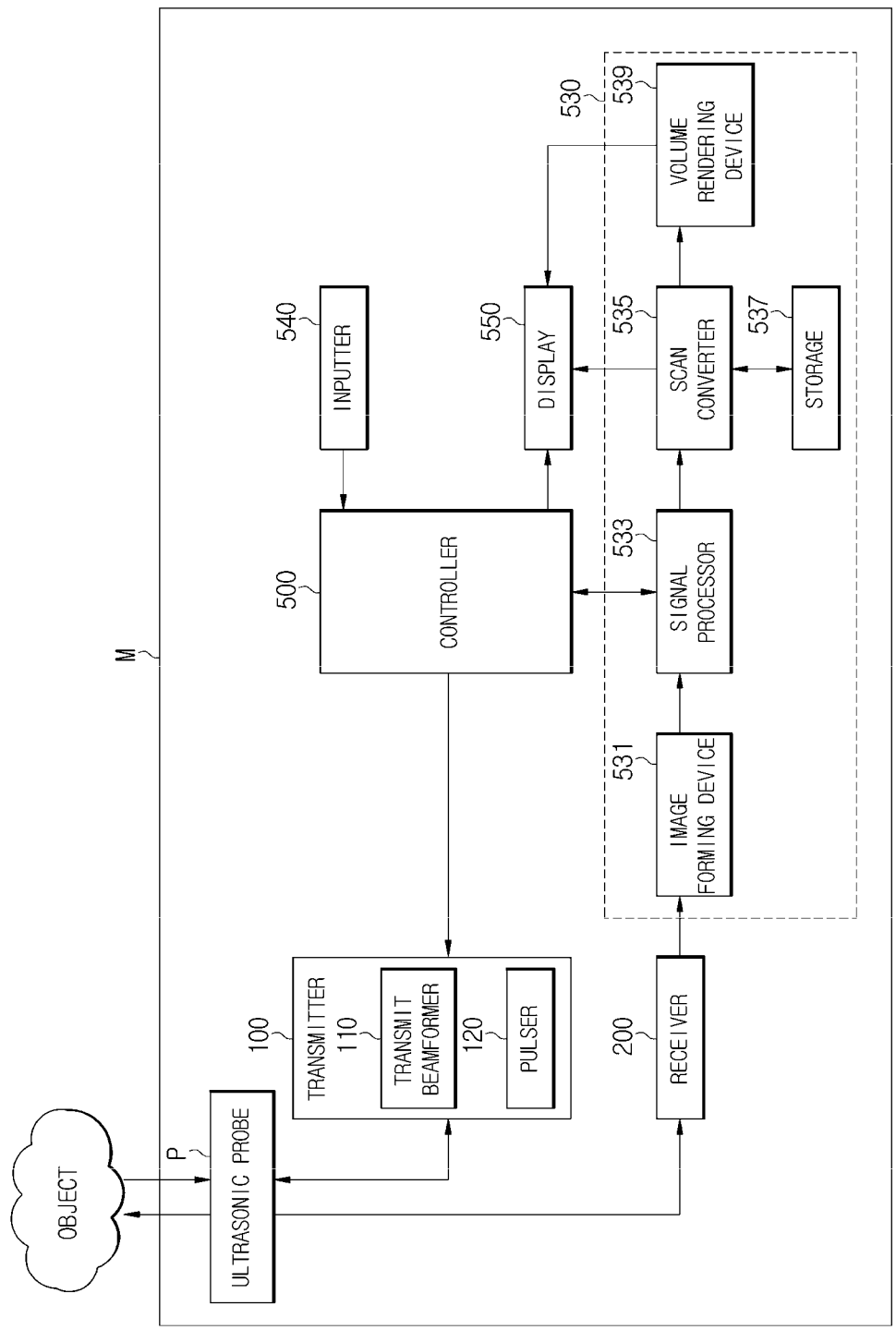
FIG. 3 is a control block diagram specifically illustrating a configuration of a main body of an ultrasonic imaging apparatus according to exemplary embodiments of the disclosure.

FIG. 1 is a view illustrating an appearance of an ultrasonic imaging apparatus according to exemplary embodiments of the disclosure, FIG. 2 is a control block diagram of an ultrasonic imaging apparatus according to exemplary embodiments of the disclosure, and FIG. 3 is a control block diagram specifically illustrating a configuration of a main body of an ultrasonic imaging apparatus according to exemplary embodiments of the disclosure.

Referring to FIG. 1, an ultrasonic imaging apparatus 1 may include an ultrasonic probe P configured to transmit ultrasonic to an object, receive an ultrasonic echo signal from the object, and convert the received ultrasonic echo signal into an electrical signal; and a main body M connected to the ultrasonic probe P and having an inputter 540 and a display 550 and configured to display an ultrasonic image. The ultrasonic probe P may be connected to the main body M of the ultrasonic imaging apparatus 1 through a cable 5 to receive various signals required for controlling the ultrasonic probe P, or transmit an analog signal or digital signal corresponding to the ultrasonic echo signal received by the ultrasonic probe P to the main body M. However, the embodiment of the ultrasonic probe P is not limited thereto, and the ultrasonic probe P may be implemented as a wireless probe to transmit and receive signals through a network formed between the ultrasonic probe P and the main body M.

The cable 5 may be connected at one end to the ultrasonic probe P and may be provided at the other end with a connector 6 that is coupled to or separated from in a slot 7 of the main body M. The main body M and the ultrasonic probe P may exchange control commands or data using the cable 5. For example, when a user inputs information about a focal depth, a size or shape of an aperture, or a steering angle through the inputter 540, the information is transmitted to the ultrasonic probe P through the cable 5 to thereby be used by a beamforming apparatus (not shown). Alternatively, when the ultrasonic probe P is implemented as a wireless probe as described above, the ultrasonic probe P is connected to the main body M through a wireless network, rather than the cable 5. Even when the main body M is connected to the main body M through a wireless network, the main body M and the ultrasonic probe P may exchange the above-described control commands or data. As illustrated in FIG. 2, the main body M may include a controller 500, an image processor 530, an inputter 540, and a display 550.

The controller 500 may controls overall operations of the ultrasonic imaging apparatus 1. In particular, the controller 500 may generate a control signal for controlling each component of the ultrasonic imaging apparatus 1, for example, a transmitter 100, a T/R switch 10, a receiver 200, an image processor 530, the display 550, and the like illustrated in FIG. 2, and may control the operations of the above-described components. In the ultrasonic imaging apparatus 1 illustrated in FIGS. 2 and 3, a transmission/reception beamformer is included in the ultrasonic probe P rather than the main body M, but the transmission/reception beamformer may be included in the main body M instead of the ultrasonic probe P.

The controller 500 may calculate delay profiles of a plurality of ultrasonic transducer elements constituting an ultrasonic transducer array TA and calculate time delay values in accordance with distance differences between each of the plurality of ultrasonic transducer elements included in the ultrasonic transducer array TA and a focal point of the object based on the calculated delay profiles. In addition, the controller 500 may control the transmission/reception beamformer in accordance therewith to generate transmission/reception signals.

The transducer array TA may be configured to be included in the main body M or the ultrasonic probe P.

Also, the controller 500 may control the ultrasonic imaging apparatus 1 by generating control commands for the respective components of the ultrasonic imaging apparatus 1 according to a user's instruction or command input through the inputter 540.

The image processor 530 may generate an ultrasonic image of a target portion inside the object based on ultrasonic signals focused by the receiver 200.

Referring to FIG. 3, the image processor 530 may include an image forming device 531, a signal processor 533, a scan converter 535, a storage 537, and a volume rendering device 539.

The image forming device 531 may generate a coherent two-dimensional (2D) image or three-dimensional (3D) image of the target portion inside the object based on the ultrasonic signals focused by the receiver 200.

The signal processor 533 may convert information on the coherent image generated by the image forming device 531 into ultrasonic image information according to a diagnosis mode, such as a brightness mode (B-mode) or a Doppler mode (D-mode). For example, when the diagnosis mode is set to the B-mode, the signal processor 533 may perform and analog/digital (A/D) conversion process, or the like and generate ultrasonic image information for a B-mode image in real time. Alternatively, when the diagnosis mode is set to the D-mode, the signal processor 533 may extract information on phase changes from the ultrasonic signal, calculate information on a blood stream corresponding to each point of cross-sectional image such as speed, power, and distribution, and generates ultrasonic image information for a D-mode image in real time.

The scan converter 535 may convert the converted ultrasonic image information received from the signal processor 533 and the converted ultrasonic image information stored in the storage 537 into general video signals for the display 550 and transmit the converted signals to the volume rendering device 539.

The storage 537 may temporarily or non-temporarily store the ultrasonic image information converted by the signal processor 533.

The volume rendering device 539 may perform volume rendering based on the video signals received from the scan converter 535, correct rendered image information to generate a final resultant image, and transmit the generated resultant image to the display 550.

The inputter 540 allows the user to input a command related to the operation of the ultrasonic imaging apparatus 1. The user may input or set an ultrasonic diagnosis start command, a diagnosis mode select command to select the B-mode, a motion mode (M-mode), the D-mode, an elastography mode (E-mode), or a 3D-mode, region of interest (ROI) setting information including size and position of a ROI, and the like through the inputter 540.

The B-mode image may refer to an image displaying the cross-section of the inside of the object and portions with strong echo signals are distinguished from portions with weak echo signals by modulating brightness. The B-mode image is generated based on information obtained from tens to hundreds of scan lines.

The M-mode may refer to an image representing changes over time in biometric information (e.g., brightness information) on a particular portion (M line) in a cross-sectional image (B-mode image). In general, the B-mode image and a M-mode image are simultaneously displayed on one screen to allow to the user to accurately diagnose by comparing and analyzing the two types of data.

The D-mode image may refer to an image of a moving object obtained by the Doppler effect in which a frequency of sound emitted from a moving object changes. Modes using the Doppler effect may further be classified into a power Doppler imaging (PDI) mode, a color flow (S Flow) mode, and a directional power Doppler imaging (DPDI) mode.

A PDI mode image may refer to an image representing the degree of Doppler signal or the number of structures (number of erythrocytes in blood). In the PDI mode, there is no aliasing signals due to less sensitivity to an angle of incidence and image attenuation caused by noise decreases. Also, since reflected Doppler energy is recorded, the PDI mode is very sensitive enabling detection of small blood vessels and blood streams with low speed.

The S Flow mode may provide a power image (PDI) representing the power of a Doppler signal in 2D distribution and a velocity image representing the velocity of the Doppler signal in 2D distribution. A S flow image may not only visualize blood streams in real time but also represent a wide range of blood stream statuses from a high velocity blood stream in a larger blood vessel to a low velocity blood stream in a smaller blood vessel.

A DPDI mode image may refer to a directional image representing information on a direction of a Doppler signal in 2D distribution in the PDI mode. Thus, the DPDI mode may detect information on blood streams more accurately than the PDI mode. In addition, the M-mode image may be generated in the D-mode.

The E-mode may refer to a method of obtaining an ultrasonic elastography image by using elastography. In this regard, elastography refers to an analysis of a phenomenon in which elasticity of tissues decreases in a hard structure such as malignant mass, and thus the degree of deformation of the tissues by pressure decreases. An ultrasonic elastography image refers to an image quantitatively representing stiffness of tissues. Particularly, the E-mode has been widely used in diagnosis of cervix cancer, breast cancer, or prostate cancer.

A 3D-mode image may refer to an image representing a geometric conformation or a space including X, Y, and Z values respectively representing depth, width, and height or a series of images indicating a stereoscopic feeling as a 3D shape or providing a stereoscopic effect. For example, the user may display a face shape of a fetus by using stereoscopic effects of the 3D-mode and provide parents of the fetus with the face shape.

Meanwhile, the operation of the disclosure may be performed in an ultrasonic contrast agent (UCA) image obtained by entering an ultrasonic contrast agent (UCA) image mode, but the disclosure is not limited to the corresponding mode, and the disclosure is not limited as long as the image of the object is derived based on the difference in the image signal.

The ultrasonic imaging apparatus 1 may operate in the B-mode for obtaining a tissue image, a low voltage B-mode for obtaining a contrast agent image and the tissue image simultaneously, a contrast agent image mode for obtaining the contrast agent image, and the contrast agent image mode prior to administration of a contrast agent.

The contrast agent image described herein may be defined as a technique for imaging by using characteristics that the echo signal reflected from microbubbles constituting the ultrasonic contrast agent (UCA) is displayed as a strong signal compared to a general tissue. A detailed description thereof will be described later.

The inputter 540 may include various devices allowing the user to input data, instructions, and commands, such as a keyboard, a mouse, a trackball, a tablet, or a touch screen module.

The display 550 may display a menu or information required for ultrasonic diagnosis, an ultrasonic image obtained during an ultrasonic diagnosis process, and the like. The display 550 may display an ultrasonic image of a target portion inside the object generated by the image processor 530. The ultrasonic image displayed on the display 550 may be a B-mode ultrasonic image, an E-mode ultrasonic image, or a 3D ultrasonic image. The display 550 may display various ultrasonic images obtained according to the aforementioned modes.

The display 550 may be implemented using various known displays such as a cathode ray tube (CRT) and a liquid crystal display (LCD).

The ultrasonic probe P may include the transducer array TA, the T/R switch 10, the transmitter 100, and the receiver 200 as illustrated in FIG. 2. The transducer array TA may be provided at one end of the ultrasonic probe P. The ultrasonic transducer array TA may refer to a one-dimensional (1D) or 2D array of a plurality of ultrasonic transducer elements 60. While the ultrasonic transducer array TA oscillates by pulse signals or alternating currents supplied thereto, ultrasonic is generated. The generated ultrasonic may be transmitted to the target portion inside the object. In this case, the ultrasonic generated by the ultrasonic transducer array TA may also be transmitted to a plurality of target portions inside the object. In other words, the generated ultrasonic may be multi-focused and transmitted to the plurality of target portions.

The ultrasonic generated by the ultrasonic transducer array TA may be reflected by the target portion inside the object and then return to the ultrasonic transducer array TA. The ultrasonic transducer array TA may receive ultrasonic echo signals returning after being reflected by the target portion. When an ultrasonic echo signal arrives at the ultrasonic transducer array TA, the ultrasonic transducer array TA may oscillate at a predetermined frequency corresponding to a frequency of the ultrasonic echo signal and output an alternating current having a frequency corresponding to the oscillation frequency. Thus, the ultrasonic transducer array TA may convert the received ultrasonic echo signal into an electric signal. Since each of the ultrasonic transducer elements 60 may output an electric signal by receiving the ultrasonic echo signal, the ultrasonic transducer array TA may output electric signals of a plurality of channels.

The ultrasonic transducer may be implemented using a magnetostrictive ultrasonic transducer using a magnetostrictive effect of a magnetic material, a piezoelectric ultrasonic transducer using a piezoelectric effect of a piezoelectric material, or a capacitive micromachined ultrasonic transducer (cMUT) that receives ultrasonic using oscillation of hundreds or thousands of micromachined thin films. In addition, any other types of transducers capable of generating ultrasonic in accordance with electric signals or generating electric signals in accordance with ultrasonic may also be used as the ultrasonic transducer.

For example, the transducer elements 60 may include a piezoelectric vibrator or a thin film. When an alternating current is supplied from a power source, the piezoelectric vibrator or the thin film vibrates at a predetermined frequency in accordance with the supplied alternating current and generates ultrasonic having the predetermined frequency in accordance with the vibration frequency. On the contrary, when an ultrasonic echo signal having a predetermined frequency arrives at the piezoelectric vibrator or the thin film, the piezoelectric vibrator or the thin film vibrates in accordance with the ultrasonic echo signal and outputs an alternating current of a frequency corresponding to the vibration frequency.

The transmitter 100 may apply transmit purses to the transducer array TA to control the transducer array TA to transmit ultrasonic signals to the target portion inside the object. The transmitter 100 may include a transmit beamformer and a pulser. A transmit beamformer 110 may generate a transmit signal pattern in accordance with a control signal of the controller 500 of the main body M and outputs the transmit signal pattern to a pulser 120. The transmit beamformer 110 may generate the transmit signal pattern based on a time delay value of each of the ultrasonic transducer elements 60 constituting the transducer array TA calculated by the controller 500 and transmit the generated transmit signal pattern to the pulser 120.

The receiver 200 may perform a predetermined processing on ultrasonic echo signals received by the transducer array TA and performs receive beamforming. The receiver 200 may include a receive signal processor and a receive beamformer.

The receiver 200 may perform image processing and signal processing after receiving a signal from the transducer. The electric signals converted by the transducer array TA are input to the receive signal processor. The receive signal processor may amplify the electric signals converted from the ultrasonic echo signals before processing the electric signals or performing time delay processing on the electric signals and may adjust gains or compensate attenuation according to depth. More particularly, the receive signal processor may include a low noise amplifier (LNA) to reduce noise of the electric signals received from the ultrasonic transducer array TA and a variable gain amplifier (VGA) to control gain values in accordance with the input signals. The VGA may be, but is not limited to, a time gain compensator (TGC) to compensate gains in accordance with distance from the focal point.

The receive beamformer may perform beamforming for the electric signals received from the receive signal processor. The receive beamformer increases intensities of the signals received from the receive signal processor through superposition. The electric signals beamformer by the receive beamformer are converted into digital signals by an A/D converter and transmitted to the image processor 530 of the main body M. When the main body M includes the A/D converter, analog signals beamformed by the receive beamformer may also be transmitted to the main body M and converted into digital signals in the main body M. Alternatively, the receive beamformer may be a digital beamformer.

The digital beamformer may include a storage to sample analog signals and store the sampled signals, a sampling period controller to control a sampling period, an amplifier to adjust a sample size, an anti-aliasing low pass filter to prevent aliasing before sampling, a bandpass filter to select a desired frequency band, an interpolation filter to increase a sampling rate while performing beamforming, a high-pass filter to remove a direct current (DC) component or a low frequency band signal, and the like.

Figure 4:
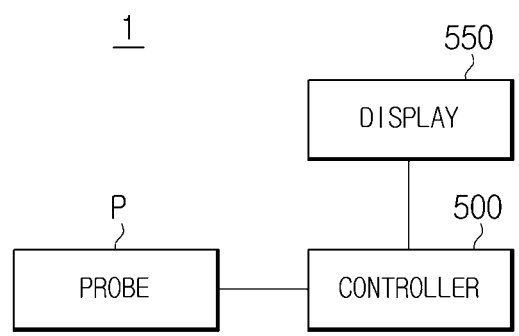
FIG. 4 is a control block diagram schematically showing the configuration of the main body of the ultrasonic imaging apparatus.

FIG. 4 is a control block diagram schematically showing the configuration of the main body of the ultrasonic imaging apparatus.

The ultrasound imaging apparatus may include a probe P, a display 550, and a controller 500.

As described above, the probe P may transmit ultrasonic waves to the object.

The probe P may receive an ultrasonic echo signal from an object and convert it into an electrical signal.

As described above, the display 550 may display menus or guides required for ultrasound diagnosis, and ultrasound images acquired during an ultrasound diagnosis process.

The controller 500 may determine the exercise cycle of the heart based on the movement of at least one valve included in the ultrasound image.

In more detail, the controller 500 may derive the position of the valve based on the ultrasound image of the heart.

The controller 500 may move the valve in correspondence with the cycle of the heart. The controller 500 may determine an exercise cycle of the heart based on the movement of the valve.

The ultrasound image of the heart may be generated as an ultrasound image including an atrium and a ventricle of the heart.

According to an embodiment, the ultrasound image of the heart may be formed as a 4CH view in which both left and right atrium and ventricle of the heart are displayed.

The controller 500 may determine the location of at least one valve based on the locations of the atrium and the ventricle of the heart.

It is separated by an atrioventricular valve (AV valve) between both atrium and ventricle.

Blood flows from the atrium to the ventricle, but does not flow back from the ventricle to the atrium.

The atrioventricular valve opens and closes in response to periodic pressure changes that occur at every heartbeat.

When the pressure in the atrium is higher than the pressure in the ventricle, the valve opens, and when the pressure in the ventricle is higher than the pressure in the atrium, the valve closes.

The atrioventricular valve between the right atrium and the right ventricle is made up of three cusps (cusps), which are connective tissues, so it can be called a tricuspid valve.

The atrioventricular valve between the left atrium and the left ventricle has two pointed processes, so it is called a bicuspid valve or a mitral valve.

In order to prevent the atrioventricular valve from being pushed up into the atrium, the valve is firmly fixed to the papillary muscle protruding from the ventricular wall by fibrous strings called chordae tendineae. The papillary muscle has nothing to do with the opening and closing of the valve, and only serves to prevent the valve from overturning by limiting its movement.

In addition to the atrioventricular valve, a valve called the semilunar valve is located between the ventricle and the artery.

The aortic valve is between the left ventricle and the aorta, and the pulmonary valve is between the right ventricle and the pulmonary artery.

These valves prevent the blood flowing out of the arteries due to ventricular contraction from flowing back in the opposite direction when the ventricle relaxes. Like the atrioventricular valve, these valves are also passively opened and closed, and the opening and closing is determined by the pressure difference between both sides of the valve.

In the present invention, in particular, an operation of determining the exercise cycle of the heart based on the movement of the meniscus provided in the atrium and ventricle will be described.

The controller 500 may identify the position of the heart valve through learning based on at least one ultrasound image of another heart.

Specifically, the controller 500 may determine the locations of the atrium and ventricle of the heart.

The controller 500 is positioned between the atrium and the ventricle of the meniscus among the above-described valves. The controller 500 may determine the positions of the atrium and the ventricle of the heart, and may determine the positions of valves positioned therebetween.

The controller 500 may determine the position of the valve of the heart based on the position of the annulus included in the heart.

The annulus corresponds to the position of the valve as described later, and the controller 500 may determine the position of the valve based on the position of the valve.

The controller 500 may form at least one at least one line corresponding to the position of the valve based on the position of the annulus.

The controller 500 may most efficiently derive the movement of the valve if one line is formed on the basis of the annulus as a part connected to the annulus.

The controller 500 may determine the movement of the valve based on the reference line.

The controller 500 may determine an ROI corresponding to the valve based on a user's command.

The controller 500 may determine the exercise cycle of the heart based on a brightness value of an ultrasound image corresponding to the region of interest.

The controller 500 may determine the region of interest corresponding to the valve as the positions of the atrium, the ventricle, and the position of the annulus as described above.

Meanwhile, the brightness value may mean a gray value derived from the M mode.

The controller 500 may determine the exercise cycle of the heart based on the amount of change in the brightness value over time.

In addition to the brightness value itself, the controller 500 may determine the movement of the valve using a time-dependent change in the brightness value, that is, a differential value.

The controller 500 may use this to determine the exercise cycle of the heart.

The ultrasound image of the heart may include a Foramen Ovale corresponding to the heart.

The foramen ovale may refer to a hole formed between the left and right atrium for the efficiency of oxygen supply to the heart.

The controller 500 may determine the exercise cycle of the heart based on the movement of the foramen ovale and the movement of the at least one valve.

The controller 500 may track a location of the heart in real time and determine a location of the at least one valve corresponding to the location of the heart.

The position of the valve can be determined based on various factors in the heart.

The position of various elements may change according to the movement of the heart.

The controller 500 may reset the position of the corresponding element by tracking the position of the heart in real time, and derive the movement of the valve based on this.

At least one component may be added or deleted corresponding to performance of the components of the ultrasound imaging apparatus illustrated in FIG. 4. In addition, it will be readily understood by those skilled in the art that mutual positions of the components may be changed to correspond to performance or structure of a system.

Meanwhile, each of the components illustrated in FIG. 4 may be a software and/or hardware component such as a Field Programmable Gate Array (FPGA) and an Application Specific Integrated Circuit (ASIC).

Figure 5:
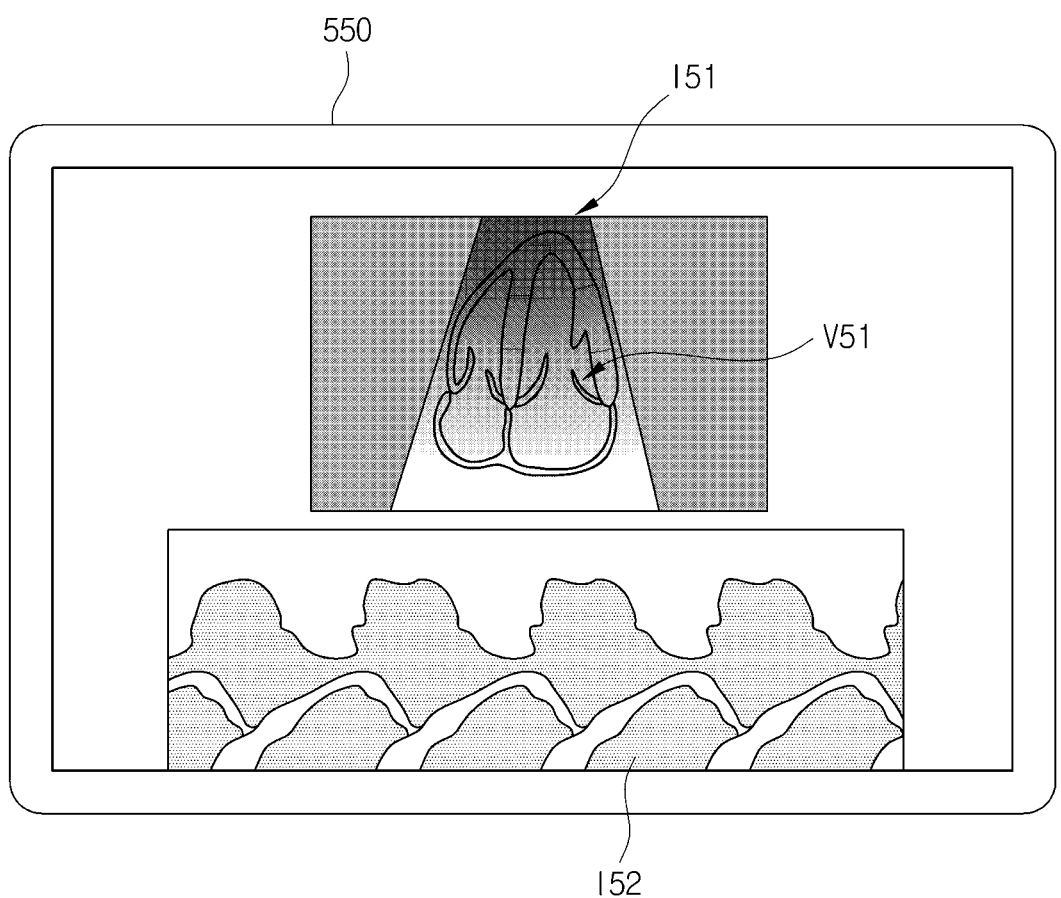
FIG. 5 is a diagram for explaining an operation of determining a heart exercise cycle based on a valve movement.

FIG. 5 is a diagram for describing an operation of determining an exercise cycle of a heart based on a movement of a valve according to an exemplary embodiment.

Referring to FIG. 5, it is shown that the display 550 of the ultrasound imaging apparatus outputs an ultrasound image (B mode, I51) and an M mode image (I52) of the heart.

It is separated by an atrioventricular valve (AV valve) between both atrium and ventricle.

Blood flows from the atrium to the ventricle, but prevents it from flowing back from the ventricle to the atrium.

The atrioventricular valve opens and closes in response to periodic pressure changes that occur at every heartbeat.

When the pressure in the atrium is higher than the pressure in the ventricle, the valve opens, and when the pressure in the ventricle is higher than the pressure in the atrium, the valve closes.

The atrioventricular valve between the right atrium and the right ventricle is called a tricuspid valve because it is made up of three cusps (cusps), which are connective tissues.

The atrioventricular valve between the left atrium and the left ventricle has two pointed processes, so it is called a bicuspid valve or a mitral valve.

In order to prevent the atrioventricular valve from being pushed up into the atrium, the valve is firmly fixed to the papillary muscle protruding from the ventricular wall by fibrous strings called chordae tendineae.

The papillary muscle has nothing to do with the opening and closing of the valve, and only serves to prevent the valve from overturning by limiting its movement.

In addition to the atrioventricular valve, a valve called the semilunar valve is located between the ventricle and the artery.

The aortic valve is located between the left ventricle and the aorta, and the pulmonary valve is located between the right ventricle and the pulmonary artery.

The valve consists of a half-moon-shaped pointed process, and according to its shape, it is called a semilunar valve.

These valves prevent the blood flowing out of the arteries due to ventricular contraction from flowing back in the opposite direction when the ventricle relaxes. Like the atrioventricular valve, these valves are also passively opened and closed, and the opening and closing is determined by the pressure difference between both sides of the valve.

The controller 500 may determine the exercise cycle of the heart based on the movement of the atrioventricular valve V51 located between the atrium and the ventricle.

Meanwhile, since the atrioventricular valve V51 is located between the atrium and the ventricle, the controller 500 may determine the positions of the atrium and the ventricle and derive the position of the valve between the atrium and the ventricle.

In addition, the controller 500 may acquire an M-mode image I52 of the region between the atrium and the ventricle, and derive the valve movement based on this.

In addition, the M-mode image I52 thus obtained may be output on the display 550 provided in the ultrasound imaging apparatus.

That is, the controller 500 may output the B-mode image I51 of the heart and simultaneously output the M-mode image I52 to the display.

The M-mode image I52 is effective in deriving motion.

The controller 500 may determine a cardiac exercise cycle by deriving a valve movement. Details related to this will be described later.

Figure 6A:
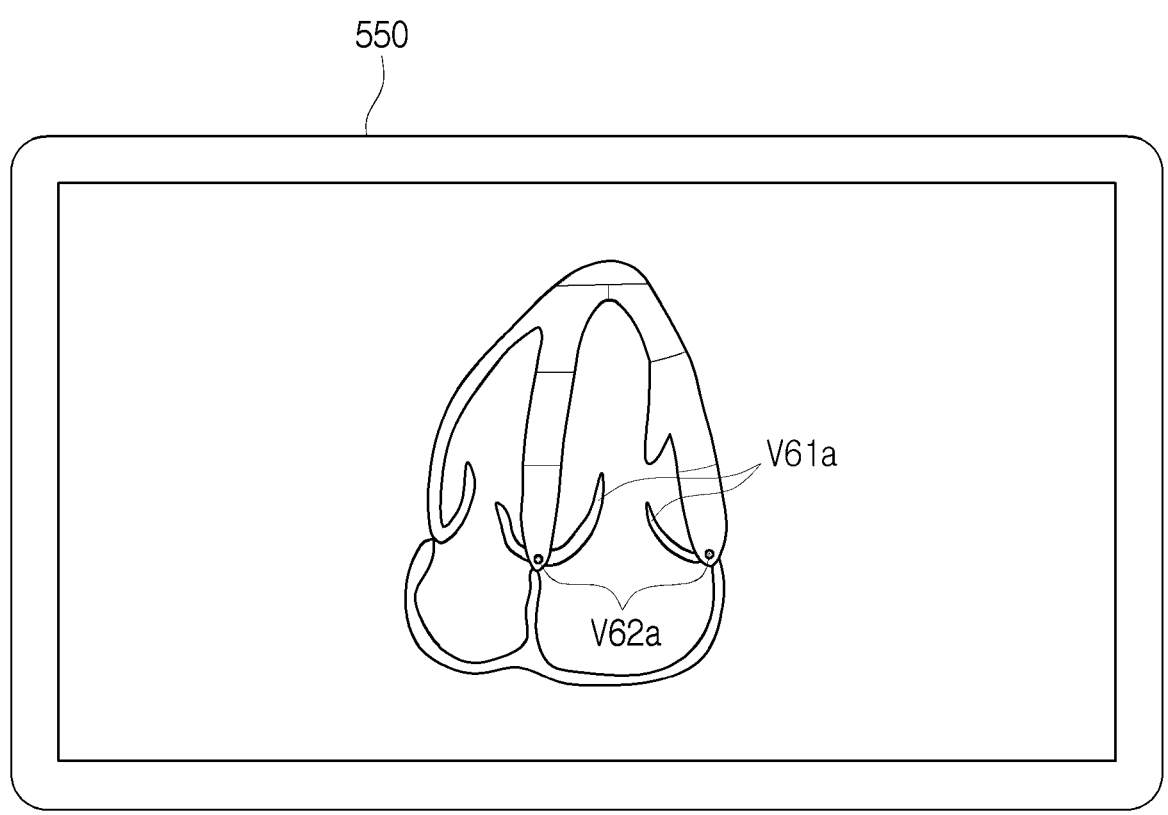
FIG. 6A is a diagram for explaining an operation of determining a position of a valve based on an annulus of a heart.

FIG. 6A is a diagram for describing an operation of determining a position of a valve based on an annulus of a heart according to an exemplary embodiment.

Figure 6B:
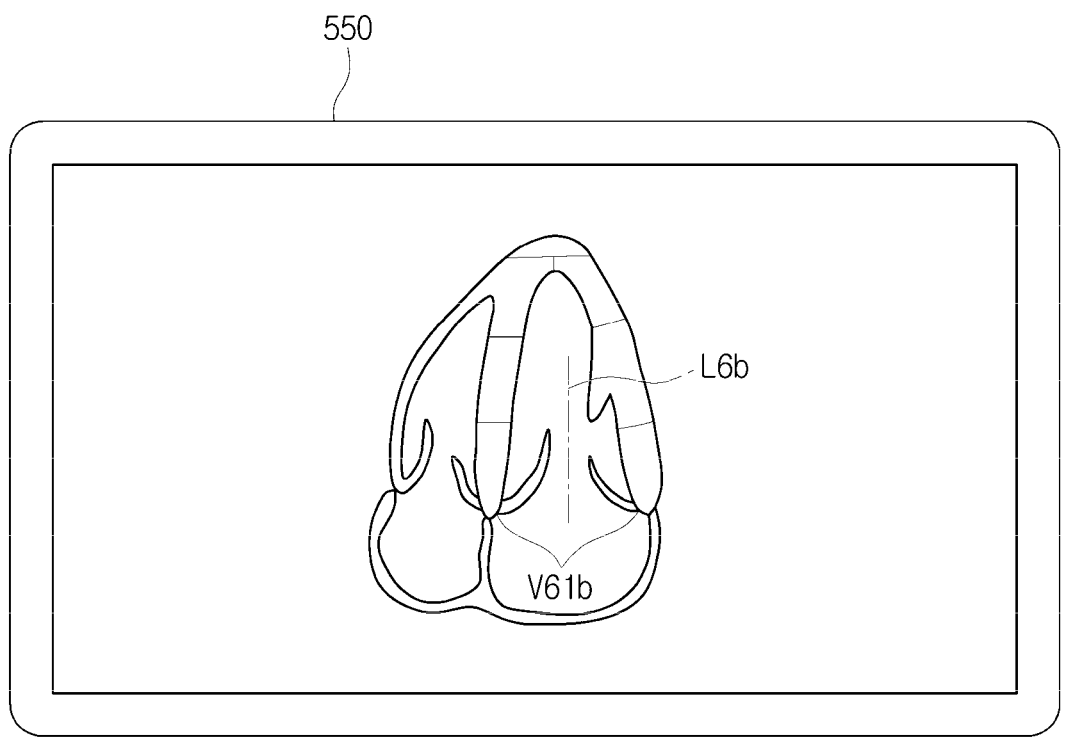
FIG. 6B is a diagram for explaining an operation of forming a line based on the position of the annulus.

FIG. 6B is a diagram illustrating an operation of forming a line based on a position of an annulus according to an exemplary embodiment.

The controller 500 may determine that the cardiac annulus V62a is a reference element for moving the bicuspid or tricuspid valve.

In addition, the annulus V62a is located between the atrium and the ventricle.

The controller 500 may be determined as a reference factor in determining the valve position and movement of the valve.

That is, even if the valve V61a moves with periodicity, the annulus V62a may serve as a reference point for movement.

The controller 500 may determine the position of the valve based on the position of the annulus V62a.

Specifically, referring to FIG. 6B, the controller 500 may form at least one line L6b based on the position of the annulus V61b. The controller 500 may derive the movement of the valve by forming at least one line L6b between the annulus and obtaining an M-mode image of the valve based on this.

In FIG. 6B, an embodiment in which a line L6b is formed in the middle between the annulus is shown, but there is no limitation on the embodiment as long as a line is formed between the annulus V61b.

Figure 7:
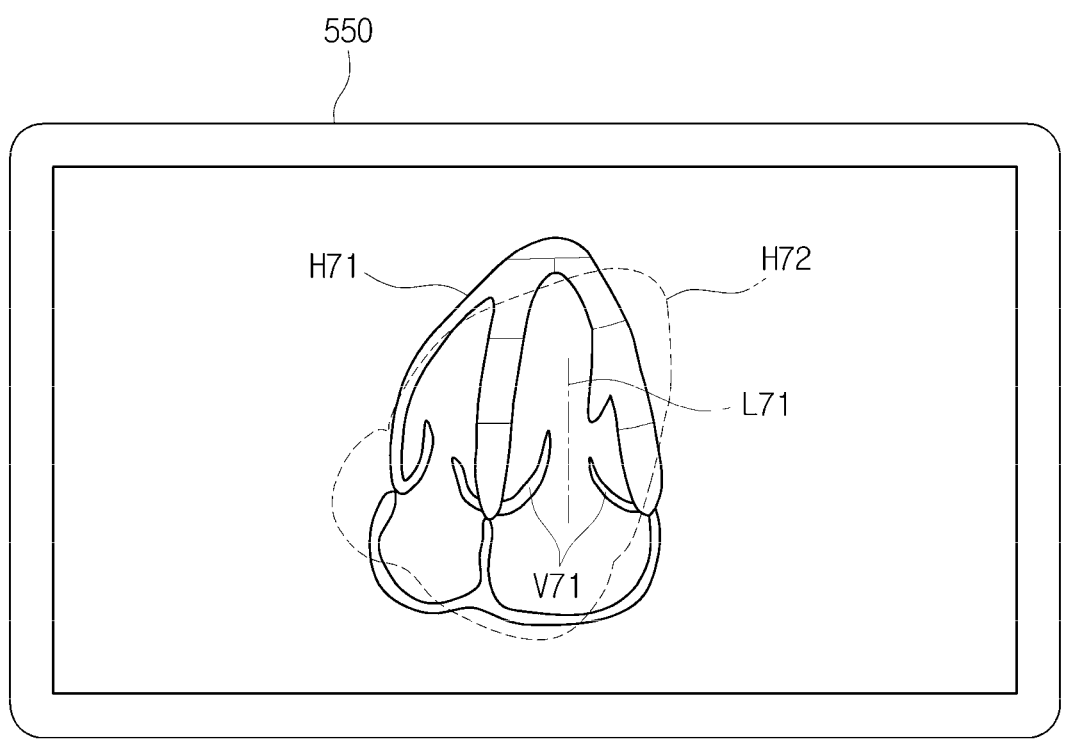
FIG. 7 is a diagram for describing an operation of an ultrasound imaging apparatus tracking a movement of a heart.

FIG. 7 is a diagram for explaining an operation of tracking a movement of a heart by an ultrasound imaging apparatus according to an exemplary embodiment.

The controller 500 according to an embodiment may track the positions of the heart (H71, H72) in real time.

The controller 500 may determine a position V71 of the at least one valve corresponding to a position on the heart.

As described above, the controller may derive the movement of the valve by using the position of the annulus.

In addition to vibrational motion, the heart can perform translational motion.

The translational motion may mean that the position of the heart itself (H71, H72) is changed.

To derive the position of the valve, it is necessary to readjust the position of the annulus.

The controller 500 may determine the position of the heart by tracking the position of the heart in real time, and determine the position of the annulus based on this.

the controller 500 may form a new line based on the re-determined position of the annulus when the position of the annulus is re-determined based on the positions of the heart (H71, H72).

The controller 500 may obtain an M-mode image of the valve to derive the movement of the valve.

The controller 500 may determine the exercise cycle of the heart based on this.

The controller 500 may form a line L71 between the annulus.

Meanwhile, the position of the annulus may be changed according to the change of the position of the heart (H71, H72).

As the position of the heart changes, the controller 500 may change the position of the line L71 between the annulus.

Meanwhile, the operation of the present invention described in FIGS. 6A, 6B and 7 is only an embodiment of the present invention, and the operation is not limited.

Figure 8A:
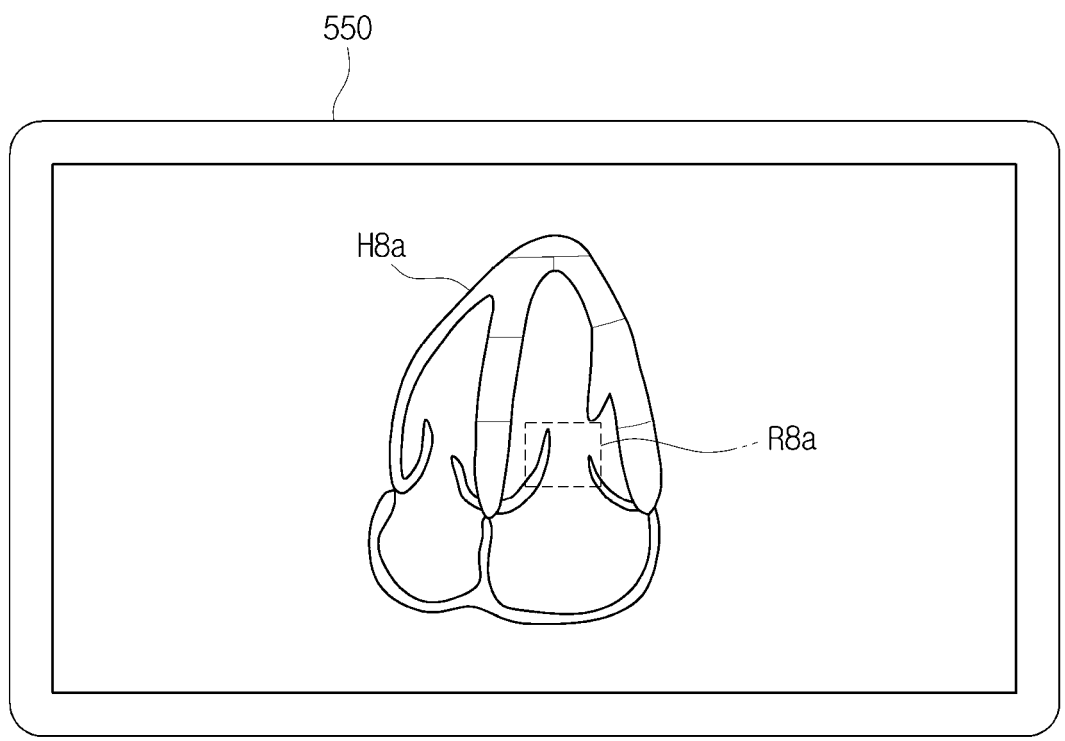
FIG. 8A is a diagram illustrating an operation of deriving a brightness value corresponding to an ROI.

FIG. 8A is a diagram illustrating an operation of deriving a brightness value corresponding to an ROI R8a according to an exemplary embodiment.

Figure 8B:
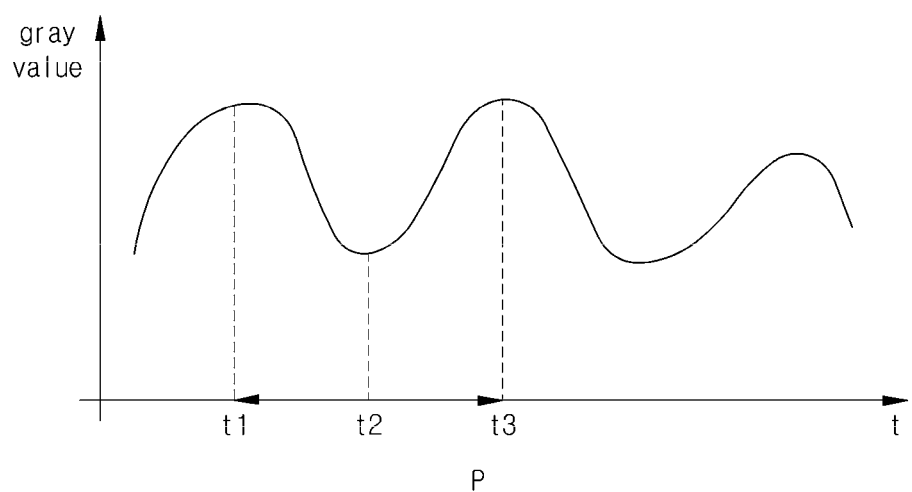
FIG. 8B is a graph showing the derived brightness values over time.

FIG. 8B is a graph showing the derived brightness values over time.

Referring to FIG. 8A, the controller may determine a region of interest R8a corresponding to the valve from the ultrasound image of the heart H8a.

The controller may determine the exercise cycle of the heart based on a brightness value of an ultrasound image corresponding to the region of interest.

Meanwhile, the region of interest may be determined by the controller based on the position between the atrium and the ventricle and the position of the annulus as described above.

Also, the region of interest R8a may be determined based on a command input by the user.

The user may determine the valve region of the heart H8a as the ROI R8a through the input unit.

Meanwhile, the controller may acquire an M-mode image of the corresponding region determined as the region of interest R8a and derive a corresponding brightness value.

Referring to FIG. 8B, a graph showing such brightness values over time is shown.

The corresponding value may be defined as the gray value of the region of interest. Meanwhile, referring to the gray value, that is, the brightness value, the brightness value is periodically changed.

The change in the brightness value of the valve may correspond to the exercise cycle of the heart.

In FIG. 8B, the brightness of the region of interest is changed with periodicity.

The controller may determine the exercise cycle of the heart using this cycle information.

The controller may derive a change amount of the brightness value over time.

That is, the controller may differentiate the brightness value according to time and may determine a point at which the derivative value becomes 0 based on this.

t1, t2 and t3 correspond to the time point.

The controller may determine the interval between t1 and t3 as one cycle of the valve movement.

Specifically, in the case of using the differential value, the controller may determine an exercise period of the valve that is twice the interval between the maximum value and the minimum value of the brightness value, and determine the exercise period of the heart.

On the other hand, the operations described in FIGS. 8A and 8B are only an exemplary embodiment of the present invention, and there is no limitation on the operation of determining the heart cycle based on the movement of the valve.

Figure 9:
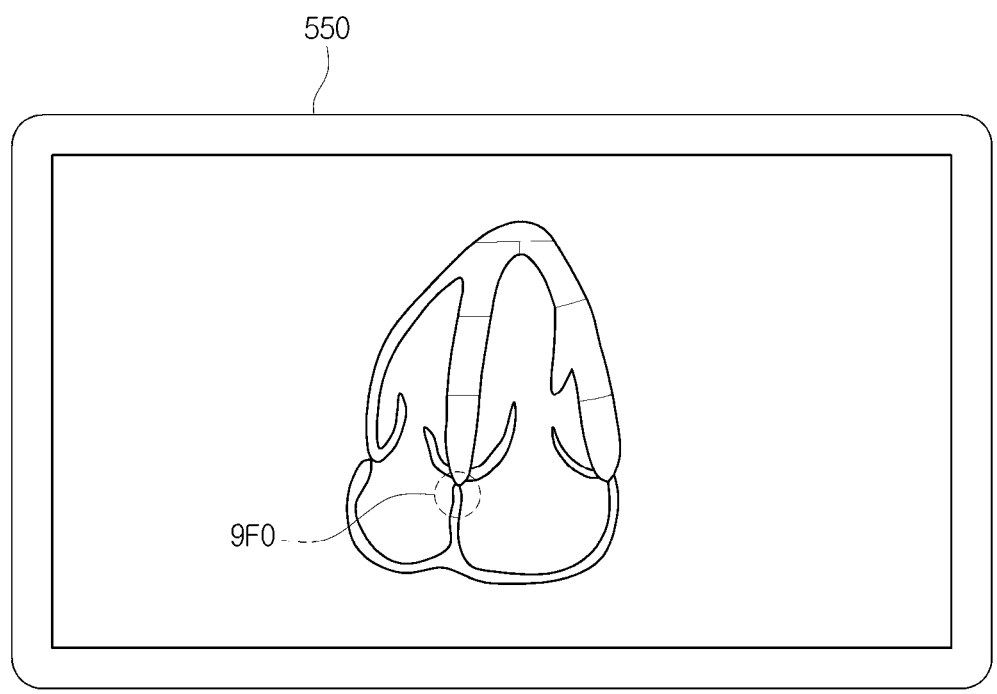
FIG. 9 is a diagram for explaining an operation of determining a heart exercise cycle based on a Foramen Ovale.

FIG. 9 is a diagram for explaining an operation of determining an exercise cycle of a heart based on a Foramen Ovale (9FO) according to an exemplary embodiment.

The foramen ovale (9FO) may mean a hole drilled between the left and right atrium to facilitate the oxygen supply of the fetus's heart.

The controller may detect that the gray value of the portion representing the foramen ovale 9FO is changed as the fetal heart moves.

The controller may determine the exercise cycle of the heart by detecting the area of the foramen ovale 9FO.

The pressure in the left atrium increases and the pressure in the right atrium drops, causing the foramen ovale (9FO) to become blocked when the fetus begins to breathe through the lungs immediately after childbirth.

The controller may determine the exercise cycle of the heart based on the above-described valve, and may determine the exercise cycle of the heart using the foramen ovale 9FO.

Meanwhile, the controller may determine the exercise cycle of the heart using the foramen ovale and may determine the exercise cycle of the heart using the valve.

In addition, the exercise cycle of the heart may be determined by comparing the exercise cycle of the heart determined based on each of the foramen ovale and the valve.

That is, the valve includes an atrioventricular valve, and as described above, the atrioventricular valve includes a bicuspid valve and a tricuspid valve.

Therefore, the controller can determine the exercise cycle of the heart based on the movements of the two atrioventricular valves and the foramen ovale.

Specifically, the controller may determine the exercise cycle of the heart based on the movement of the bicuspid valve.

The controller may determine the exercise cycle of the heart based on the movement of the tricuspid valve, and may determine the exercise cycle of the heart based on the movement of the foramen ovale.

In addition, the controller may compare each exercise cycle with each other and determine whether the exercise cycle of the heart derived based on each is valid.

The controller may determine that the exercise cycle of the heart is valid if the exercise cycle of the heart determined based on each of the valve and the foramen ovale has a similar value within a predetermined range.

The controller is determined based on the tricuspid valve when the heart cycle determined on the basis of the bicuspid valve and the foramen ovale is substantially the same, but the heart cycle determined on the basis of the tricuspid valve is large from that of the heart determined based on the bicuspid valve and the foramen ovale. The exercise cycle of the heart can be excluded in determining the exercise cycle.

The controller may determine an exercise cycle of the heart based on the movement of the valve.

On the other hand, determining the exercise cycle of the heart using the foramen ovale is only an embodiment of the present invention.

There is no limit to the operation of determining the movement cycle of the heart by using the movement of an identifiable element in the ultrasound image of the heart.

FIG. 10 is a flow chart according to an embodiment.

Referring to FIG. 10, the ultrasound imaging apparatus may acquire an ultrasound image of a heart through a probe 1001.

Also, the ultrasound imaging apparatus may determine the position of the valve based on the acquired ultrasound image 1002.

Meanwhile, the ultrasound imaging apparatus may determine an exercise cycle of the heart based on the movement of the valve 1003.

Meanwhile, the ultrasound imaging apparatus may output an M-mode image of the movement of the valve and a movement cycle of the heart to the display of the ultrasound imaging apparatus 1004.

Meanwhile, the disclosed exemplary embodiments may be implemented in the form of a recording medium storing instructions that are executable by a computer. The instructions may be stored in the form of a program code, and when executed by a processor, the instructions may generate a program module to perform operations of the disclosed exemplary embodiments. The recording medium may be implemented non-transitory as a computer-readable recording medium.

The non-transitory computer-readable recording medium may include all kinds of recording media storing commands that can be interpreted by a computer. For example, the non-transitory computer-readable recording medium may be, for example, ROM, RAM, a magnetic tape, a magnetic disc, flash memory, an optical data storage device, etc.

Embodiments of the disclosure have thus far been described with reference to the accompanying drawings. It will be obvious to those of ordinary skill in the art that the disclosure may be practiced in other forms than the embodiments as described above without changing the technical idea or essential features of the disclosure. The above embodiments are only by way of example, and should not be interpreted in a limited sense.

What is claimed is:

1. An ultrasonic imaging apparatus comprising:
a display;
a probe configured to acquire an ultrasound signal of a heart; and
a controller configured to:
generate an ultrasound image of the heart based on the ultrasound signal;
control the display to display the ultrasound image of the heart, wherein the ultrasound image of the heart comprises an atrium, a ventricle, an annulus and a foramen ovale of the heart;
determine an exercise cycle of the heart based on a movement of at least one valve and a movement of the foramen ovale included in the ultrasound image;
determine a region of interest corresponding to the at least one valve based on a position of the atrium, a position of the ventricle and a position of the annulus;
determine the exercise cycle of the heart based on a change amount of a brightness value of the region of interest corresponding to the at least one valve;
detect an area corresponding to the foramen ovale from the ultrasound image;
determine the exercise cycle of the heart based on a change amount of a brightness value of the area corresponding to the foramen ovale; and
compare, the exercise cycle of the heart determined by the change amount of the brightness value of the region of interest corresponding to the at least one valve and the exercise cycle of the heart determined by the change amount of the brightness value of the area corresponding to the foramen ovale, to determine whether the exercise cycle of the heart determined by the change amount of the brightness value of the region of interest corresponding to the at least one valve is valid.

2. The ultrasonic imaging apparatus according to claim 1, wherein the controller is configured to identify the region of interest corresponding to the at least one valve of the heart through machine learning trained based on a plurality of ultrasound images of at least one other heart.

3. The ultrasonic imaging apparatus according to claim 1, wherein the controller is configured to:
generate at least one line corresponding to a position of the at least one valve based on the position of the annulus; and
determine the movement of the at least one valve based on the at least one line.

4. The ultrasonic imaging apparatus according to claim 1, wherein the controller is configured to:
determine the region of interest corresponding to the at least one valve based on a user's command.

5. The ultrasonic imaging apparatus according to claim 1, wherein the controller is configured to:
track a position of the heart in real time; and
determine a position of the at least one valve corresponding to the position of the heart.

6. A method of controlling an ultrasonic imaging apparatus comprising:
acquiring an ultrasound signal of a heart;
generating an ultrasound image of the heart based on the ultrasound signal, wherein the ultrasound image of the heart comprises an atrium, a ventricle, an annulus and a foramen ovale of the heart;
controlling a display to display the ultrasound image of the heart; and
determining an exercise cycle of the heart based on a movement of at least one valve included in the ultrasound image,
wherein the determining of the exercise cycle of the heart comprises:
determining a region of interest corresponding to the at least one valve based on a position of the atrium, a position of the ventricle and a position the annulus;
determining the exercise cycle of the heart based on a change amount of a brightness value of the region of interest corresponding to the at least one valve;
detecting an area corresponding to the foramen ovale from the ultrasound image;
determining the exercise cycle of the heart based on a change amount of a brightness value of the area corresponding to the foramen ovale; and
comparing, the exercise cycle of the heart determined by the change amount of the brightness value of the region of interest corresponding to the at least one valve and the exercise cycle of the heart determined by the change amount of the brightness value of the area corresponding to the foramen ovale, to determine whether the exercise cycle of the heart determined by the change amount of the brightness value of the region of interest corresponding to the at least one valve is valid.

7. The ultrasonic imaging apparatus method according to claim 6, further comprising:

identifying the region of interest corresponding to the at least one valve of the heart through machine learning trained based on a plurality of ultrasound images of at least one other heart.

8. The method according to claim 6, further comprising:
generating at least one line corresponding to position of the at least one valve based on the position of the annulus,
wherein the determining the region of interest corresponding to the at least one valve comprises:
determining the movement of the at least one valve based on the at least one line.

9. The method according to claim 6, wherein the determining the region of interest corresponding to the at least one valve comprises:
determining the region of interest corresponding to the at least one valve based on a user's command.

10. The method according to claim 6, further comprising:
tracking a position of the heart in real time; and
determining a position of the at least one valve corresponding to the position of the heart.

\* \* \* \* \*